(12) United States Patent
Adenmark

(10) Patent No.: US 9,763,672 B2
(45) Date of Patent: Sep. 19, 2017

(54) FEMORAL COMPRESSION DEVICE

(75) Inventor: Tobias Adenmark, Uppsala (SE)

(73) Assignee: ST. JUDE MEDICAL COORDINATION CENTER BVBA, Zaventem (BE)

( * ) Notice: Subject to any disclaimer, the term of this patent is extended or adjusted under 35 U.S.C. 154(b) by 542 days.

(21) Appl. No.: 13/397,047

(22) Filed: Feb. 15, 2012

(65) Prior Publication Data

US 2012/0215252 A1    Aug. 23, 2012

Related U.S. Application Data

(60) Provisional application No. 61/445,875, filed on Feb. 23, 2011.

(51) Int. Cl.
*A61B 17/135*    (2006.01)
*A61B 17/132*    (2006.01)
*A61B 17/00*    (2006.01)

(52) U.S. Cl.
CPC ........ *A61B 17/135* (2013.01); *A61B 17/1325* (2013.01); *A61B 2017/00902* (2013.01)

(58) Field of Classification Search
CPC . A61B 17/1325; A61B 17/135; A61B 17/132; A61B 17/1322; A61B 17/12; A61B 17/1355; A61B 2017/00902; A61B 2017/12004; A61F 5/30; A61F 5/32; A61F 5/34; A61H 39/04
USPC .... 606/201–204.55, 192–196; 600/207, 499, 600/37, 29, 31
See application file for complete search history.

(56) References Cited

U.S. PATENT DOCUMENTS

| | | | | |
|---|---|---|---|---|
| 3,595,225 A | * | 7/1971 | Beeman | 602/21 |
| 4,479,495 A | * | 10/1984 | Isaacson | 606/204 |
| 4,557,262 A | * | 12/1985 | Snow | 606/201 |
| 4,997,438 A | * | 3/1991 | Nipper | 606/201 |
| 5,295,996 A | * | 3/1994 | Blair | 606/203 |
| 5,307,811 A | * | 5/1994 | Sigwart et al. | 600/490 |
| 5,312,350 A | * | 5/1994 | Jacobs | 604/116 |
| 5,542,427 A | * | 8/1996 | Åkerfeldt | 600/490 |
| 5,681,340 A | * | 10/1997 | Veronikis | 606/191 |
| 5,792,173 A | * | 8/1998 | Breen et al. | 606/201 |
| 5,873,890 A | * | 2/1999 | Porat | 606/201 |
| 6,264,673 B1 | * | 7/2001 | Egnelov | A61B 17/135 128/887 |
| 6,827,727 B2 | * | 12/2004 | Stålemark et al. | 606/201 |

(Continued)

FOREIGN PATENT DOCUMENTS

DE    44 24 838 A1    1/1996
EP    0 462 088 A2    12/1991

(Continued)

*Primary Examiner* — Christopher L Templeton
(74) *Attorney, Agent, or Firm* — Foley & Lardner LLP

(57) ABSTRACT

A femoral compression device (11) for compressing a femoral artery (12) of a patient, having a base plate (13) provided with two opposing extensions, each of the two opposing extensions having a member for affixing a belt (14), which is adapted to be arranged around a patient's body, an inflatable air cushion (15), provided with a back plate (19), for compressive bearing against a puncture site, and a pump (16) connected to the inflatable air cushion for inflation of the air cushion. The femoral compression device further comprises a spacer (18) having a height and being adapted to be mounted between the inflatable air cushion and the base plate.

12 Claims, 4 Drawing Sheets

(56) References Cited

U.S. PATENT DOCUMENTS

| | | | |
|---|---|---|---|
| 7,329,270 B2 | 2/2008 | Åkerfeldt et al. | |
| 2004/0243044 A1* | 12/2004 | Penegor | A61B 17/0057 602/48 |
| 2010/0280541 A1* | 11/2010 | Lampropoulos et al. | 606/203 |

FOREIGN PATENT DOCUMENTS

| | | |
|---|---|---|
| EP | 1 386 586 A1 | 2/2004 |
| EP | 1 402 825 A2 | 3/2004 |

* cited by examiner

FEMORAL COMPRESSION DEVICE

The right of priority is claimed under 35 U.S.C. §119(e) based on U.S. Provisional Application Ser. No. 61/445,875, filed Feb. 23, 2011, the entire contents of which, including the specification, drawings, claims and abstract, are incorporated herein by reference.

FIELD OF THE INVENTION

The present invention relates generally to a femoral compression device and in particular to a femoral compression device comprising a pressurizing arrangement adaptable to varying body constitutions of a patient.

BACKGROUND OF THE INVENTION

Femoral compression devices for applying pressure on a patient's femoral artery after completion of an interventional procedure are known. An example of such a femoral compression device is disclosed in the patents U.S. Pat. No. 5,307,811 and EP 0 462 088, which are assigned to the present assignee and whose contents are incorporated herein by reference for the compression devices and methods disclosed therein.

A femoral compression device according to these publications comprises basically a pressurizing means for compressive bearing against a puncture site at a femoral artery of a patient, a belt adapted to be fixed around the patient's body, and a base plate supporting the pressurizing means and being provided with two extensions. In use, the pressurizing means, which e.g. has the form of an inflatable semi-spherical air cushion, is positioned over the femoral artery, and the belt, which extends from the end of the first extension, around the patient's body and to the end of the second extension, is tightened. To apply pressure on the femoral artery, the inflatable semi-spherical air cushion is inflated by a pump to a certain predetermined pressure, which is read from a pressure gauge.

The air cushion may be a replaceable air cushion unit preferably packaged in a sterile package to minimize the risk of contamination of a part which is in contact with an area on a patient's body, and which can be exposed to the risk of infection. An example of such a device is disclosed in U.S. Pat. No. 5,542,427, which is assigned to the present assignee and whose contents are incorporated herein by reference for the compression devices and methods disclosed therein.

In use, the inflatable air cushion is positioned over a femoral artery of a patient, and the belt, which extends from the end of the first extension, around the patient's body and to the end of the second extension, is tightened. Then, the inflatable air cushion is inflated by a hand pump to a certain internal pressure, thereby expanding the air cushion such that the femoral artery is compressed in order to prevent bleeding through a puncture hole being made in the artery wall. The internal pressure, which can be read from a pressure gauge provided on the pump, should be raised to a value between the diastolic pressure and the systolic pressure—which is a procedure that has proven to work very well for the vast majority of patients.

SUMMARY OF THE INVENTION

An inherent characteristic of a pneumatic device, and in particular of the inflatable air cushion described above, is that the internal pressure only within a certain operating range corresponds to an increased length of stroke (i.e. increased expansion of the air cushion). For a pressurizing means in the form of an inflatable air cushion, this feature implies that when the air cushion has reached its maximal expansion, a further increase of the internal pressure does not expand the air cushion any more, which, in turn, means that no more compression pressure can be applied on the femoral artery. Normally, i.e. for the vast majority of patients having a normal or ordinary body constitution, this is of no problem since the stroke length (i.e. the expansion) of the air cushion corresponds to the expansion needed to completely, or almost completely, compress the artery such that the flow of blood therethrough is significantly reduced, to thereby prevent bleeding from the puncture wound. In other words, the operating range of the air cushion ranges from a minimum value where the flow of blood is essentially unrestricted to a maximum value where the flow of blood is essentially completely stopped.

However, for those patients where the femoral artery is embedded in a very thick layer of adipose tissue, it can be difficult to determine whether the air cushion has reached its maximal expanded state, in which no more compression of the femoral artery is possible. And when a pressure gauge is used, this problem is even more pronounced because the pressure gauge continues to show increasing values even though the air cushion has reached its maximal expansion. This behavior may give an inexperienced user a deceitful impression that the compression pressure on the femoral artery actually is increasing. Needless to say, such a misjudgment may give rise to very serious complications.

Certain embodiments of the invention are therefore directed to an improved femoral compression device, and one general object of such embodiments is to provide such a compression device for use on patients with a thick layer of adipose tissue at the site of an open puncture in the femoral artery or other blood vessel.

Embodiments of the invention are directed to a femoral compression device, for use on patients with an excessive amount of adipose tissue in the lower torso region, comprising an inflatable air cushion, a pump, a belt adapted to be fixed around the patient's body, and a base plate supporting the pressurizing device and being provided with two extensions. According to one embodiment of the present invention the inflatable air cushion is raised from the base plate by mounting a spacer between the base plate and the air cushion. This effectively moves the range of expansion of the air cushion away from the base plate, pressing the excessive adipose tissue to the sides, and ensuring proper access to the compression site. In use the inflatable semi-spherical air cushion is positioned over the femoral artery, and the belt, which extends from the end of the first extension, around the patient's body and to the end of the second extension, is tightened. To apply pressure on the femoral artery, the inflatable semi-spherical air cushion is inflated by a pump effectively compressing the artery such that the flow of blood therethrough is significantly reduced, to thereby prevent bleeding from the puncture wound.

DETAILED DESCRIPTION OF PREFERRED EMBODIMENTS

Figure 1:
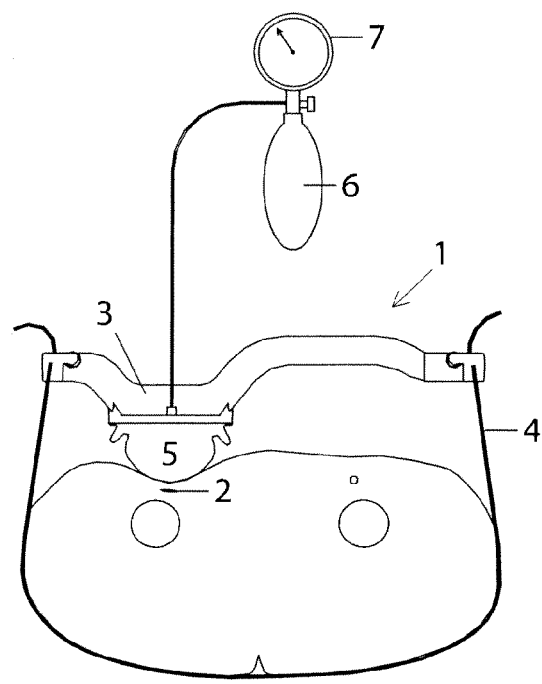
FIG. 1 is a cross-sectional view of a previously proposed femoral compression device attached to the body of a patient having a normal amount of adipose tissue overlying a femoral artery.

FIG. 1 illustrates how a previously proposed femoral compression device 1 is attached to the body of a patient in order to apply compression pressure on a femoral artery 2 in which a puncture hole has been made. The compression device 1 comprises basically a base plate 3, a belt 4 and an inflatable air cushion 5, which can be inflated by a pump 6, which is provided with a pressure gauge 7.

The patient illustrated in FIG. 1 has a normal body constitution, with an average amount of adipose tissue being localized between the skin and the femoral artery 2. When in a semi-inflated state, i.e. less than fully expanded, the air cushion 5 can therefore compress the artery 2 such that no blood penetrates through the puncture hole in the femoral artery 2. Herein, the expression "normal body constitution" refers to a body constitution to which this existing femoral compression device 1 is adapted, i.e. the stroke length (the expansion) of the air cushion 5 is sufficient for the pressure force being applied therewith to be transmitted through the layer of adipose tissue and compress the femoral artery 2.

Figure 2:
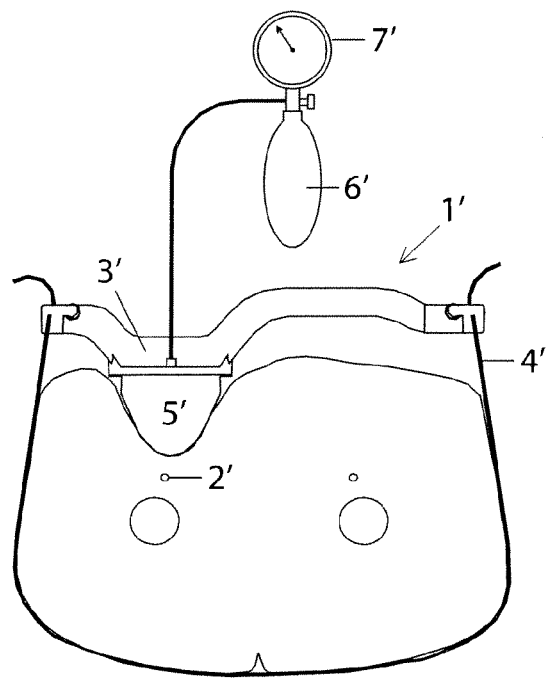
FIG. 2 is a cross-sectional view of a previously proposed femoral compression device attached to the body of a patient having an excessive amount of adipose tissue overlying a femoral artery.

Another case is illustrated in FIG. 2, where a femoral compression device 1' has been attached to the body of an overweight patient to apply compression pressure on a femoral artery 2' in which a puncture hole has been made. The femoral compression device 1' of FIG. 2 is identical to the femoral compression device 1 shown in FIG. 1, and comprises basically a base plate 3', a belt 4' and an inflatable air cushion 5', which can be inflated by a pump 6', which is provided with a pressure gauge 7'. In this case, an excessive amount of adipose tissue is localized between the skin and the femoral artery 2', essentially filling up the space within the boundaries defined by the base plate, the belt and the air cushion. This previously proposed femoral compression device 1' was not designed for this type of patient, and, as is illustrated in the figure, even in the fully expanded state, the air cushion 5' cannot compress the femoral artery 2' enough to stop bleeding through the puncture hole therein. In particular it should be noted that pressure gauges 7 and 7' display the same internal pressure for the two cases illustrated in FIG. 1 and FIG. 2, respectively.

As discussed above, a further inflation of the air cushion 5' of FIG. 2 results only in an increase in the internal pressure within the air cushion 5', without any more compression pressure being applied on the femoral artery 2'. Furthermore, the read-out from the pressure gauge 7' will—at least in some sense—support and justify such an operation by the user, because the pressure gauge 7' will continue to show increasing values and thereby give the user the impression that more compression pressure actually is being applied on the femoral artery 2'. In short: when in a not fully expanded state (as in FIG. 1), more compression pressure is actually applied on the femoral artery 2 when the air cushion 5 is inflated by the pump 6, which is in accordance with the readings from the pressure gauge 7; whereas in a fully expanded state (as in FIG. 2), no more compression pressure is applied on the femoral artery 2' when the air cushion 5' is inflated by the pump 6', which is in contradiction to the readings from the pressure gauge 7'.

In the situation illustrated in FIG. 2, an inexperienced user may continue to operate the pump 6' in a (vain) attempt to apply more compression pressure on the femoral artery 2', and when the user realizes that the bleeding is not going to stop, there is a risk that the decision will be that the compression device 1' has been misplaced and has to be moved to another position, which leads to unnecessary bleeding. Here it should be mentioned that extra tightening of the belt 4' to some extent could compensate for the above-mentioned disadvantage of the known femoral compression device 1'. However, this procedure requires careful consideration by the user, and the risk of a misleading reading from the pressure gauge 7' is still present. In addition, in those patients where the excess adipose tissue completely or almost completely fills up the space within the boundaries of the base plate, the belt and the air cushion (as illustrated in FIG. 2), further tightening of the belt is not possible.

Figure 3:
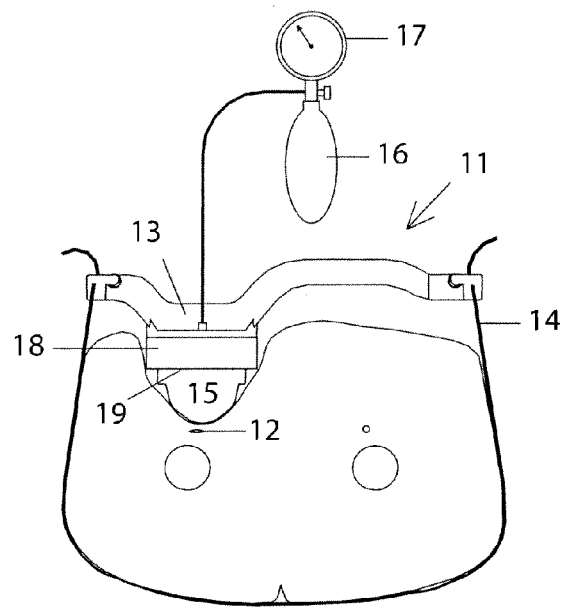
FIG. 3 illustrates a first embodiment of a femoral compression device according to the present invention.

Experience from manual compression (performed by a nurse or other medical practitioner) of obese patients has shown that when initializing the procedure, the person performing the compression needs to penetrate his or her hand deep into the folds of the adipose tissue. According to embodiments of the present invention, a spacer is arranged between the back plate and the air cushion in order to extend the penetration depth of the device into excess adipose tissue, thereby enabling both a considerably improved starting point and working conditions for the procedure. In FIG. 3 is illustrated a femoral compression device 11 according to an embodiment of the present invention. The device comprises a base plate 13, a belt 14 and an inflatable air cushion 15, which can be inflated by a pump 16, which is provided with a pressure gauge 17. The air cushion is provided with a back plate 19 at the side facing the base plate. Further, the device is provided with a spacer 18 having a height, adapted to be mounted between the inflatable air cushion and the base plate 13. That is achieved by attaching the spacer to the base plate and to the back plate of the air cushion. The spacer is attached to the base plate in a removable manner. The spacer is attached to the back plate in a removable manner. As seen in FIG. 3, at the starting point of the procedure, i.e. when the device 11 has been secured to the patient with the belt 14 and the air cushion is yet to be inflated, the excess adipose tissue has been pressed aside due to the extension of the compression component by use of the spacer.

The femoral compression device 11 may be assembled in connection with usage by mounting the spacer to the base plate and then attaching the air cushion to the spacer. The pump is also connected to the air cushion. As an alternative some, or all, parts may be assembled in advance and the femoral compression device, provided with the spacer, is directly ready to be used. This is applicable to all embodiments mentioned herein.

Figure 4A:
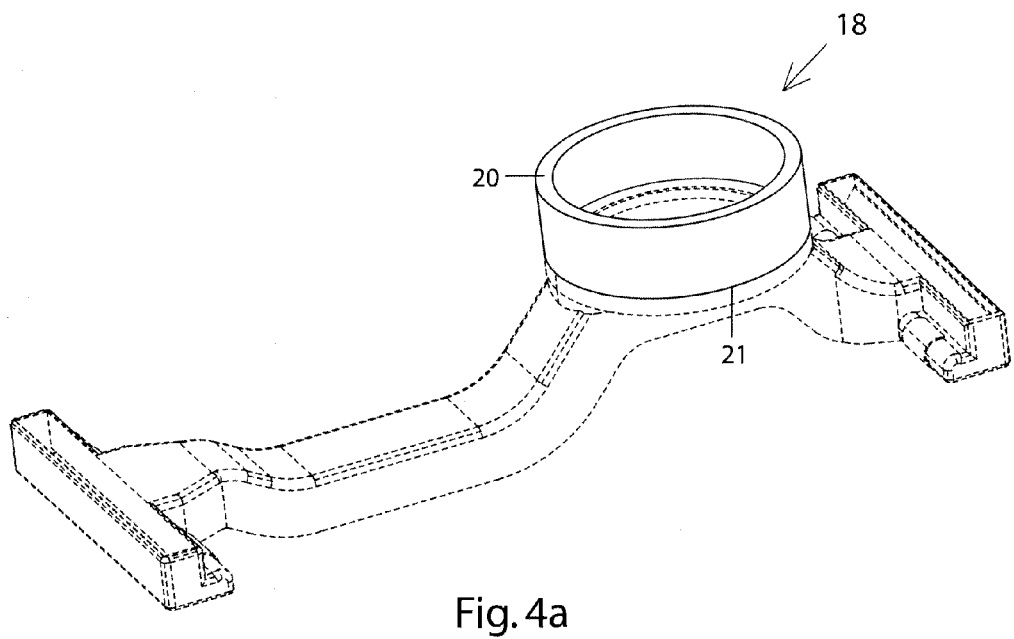
FIGS. 4a-4d illustrate perspective views of different embodiments of the spacer according to embodiments of the present invention.

Preferably, the spacer 18 has an essentially circular-cylindrical shape with a cylinder wall having first and second edges 20, 21 (see FIG. 4a), wherein the first edge 20 is adapted to be attached to the back plate 19 of the air cushion and the second edge 21 is adapted to be attached to the base plate 13.

However, other cross-sectional shapes of the spacer are naturally possible within the scope of the claims as long as the intended purpose of the spacer is achieved, i.e. enabling the air cushion to be arranged at a more distant level in relation to the base plate such that the desired pressure is applied to the femoral artery. The cross-sectional shape may e.g. be elliptical or rectangular as long as it may be attached to the base plate and the back plate of the air cushion.

The spacer is preferably made from a transparent material in order see the wound site when positioning the air cushion in relation to the femoral artery.

For the same purpose the spacer may be provided with at least one opening 23 in the cylinder wall. In addition, the tubing from the pump to the air cushion may be led through the opening.

Figure 4B:
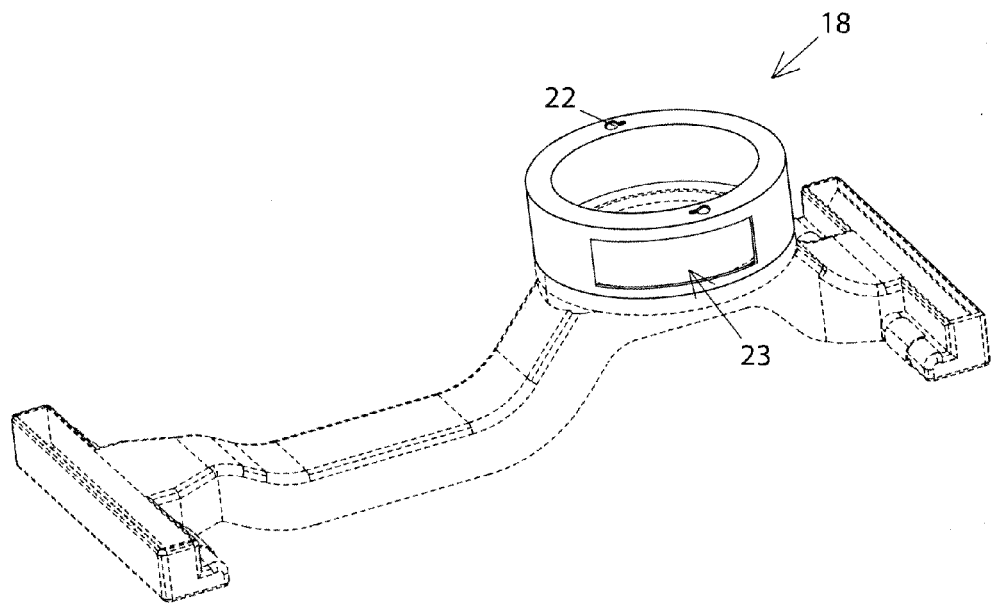
Figure 4C:
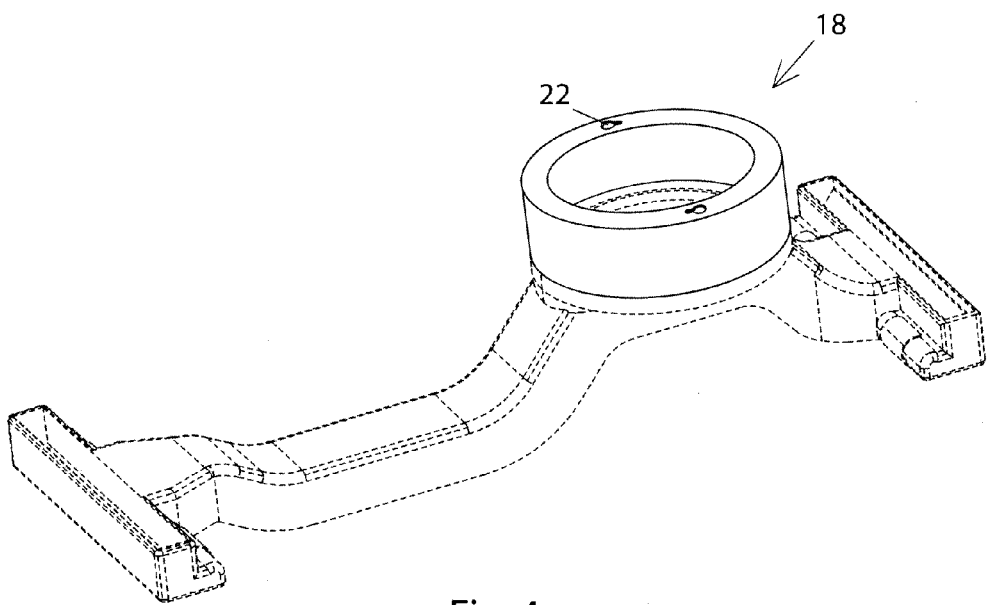
Figure 4D:
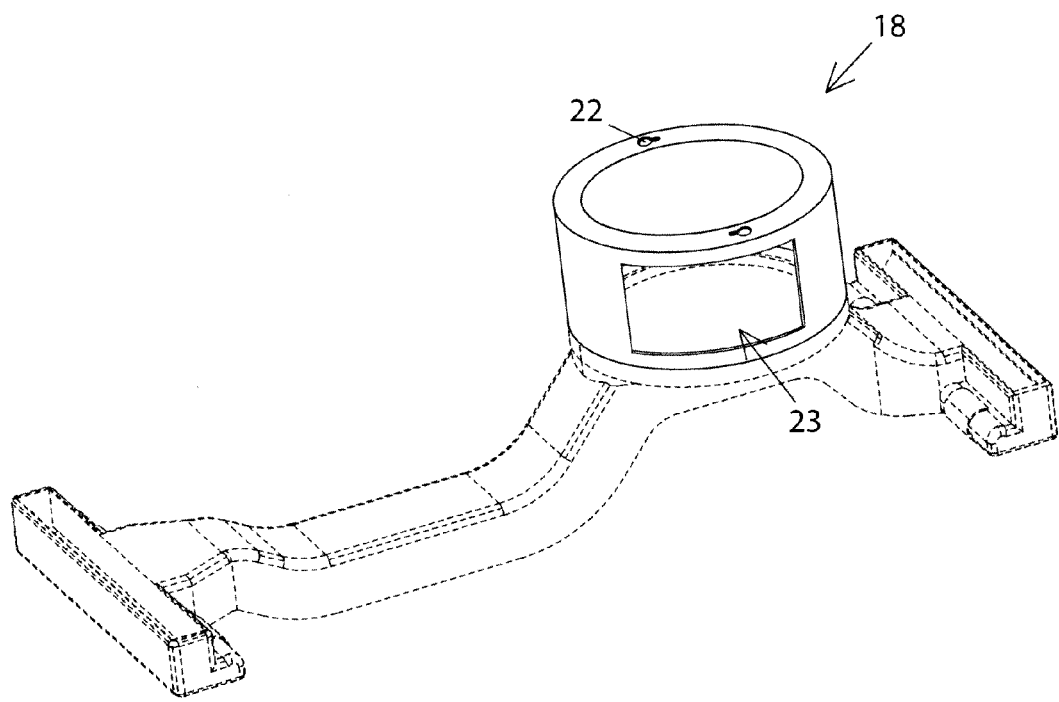

Two spacers having different heights and provided with an opening 23 are illustrated in FIGS. 4b and 4d.

The cylinder wall may have a thinner thickness compared to the thickness at the edges which improves the visibility of the wound if the spacer is made from a transparent material.

The first and second edges are each provided with at least one attachment member 22 for cooperation with mating attachment members at the base plate and back plate, respectively. The attachment member 22 may e.g. be a mating hole (to mate with a knob) which is illustrated in FIGS. 4b-4d.

Alternatively, the attachment members are realized by a bayonet or any other type of joint.

In still another embodiment the spacer is attached to the base plate and the back plate by an adhesive, e.g. by a self-adhesive at each of the edges that is covered by a plastic foil that is peeled off when the spacer is to be mounted to the base plate and back plate.

The height of the spacer is preferably in the range of 10-100 mm (for example, 10 mm, 20 mm, 30 mm, 40 mm, 50 mm, 60 mm, 70 mm, 80 mm, 90 mm, or 100 mm). Even larger heights may be applicable for really obese patients. A set of spacers having different heights may be provided in a kit including e.g. five different spacers having heights of e.g. 10, 30, 50, 80 and 100 mm.

Figure 5:
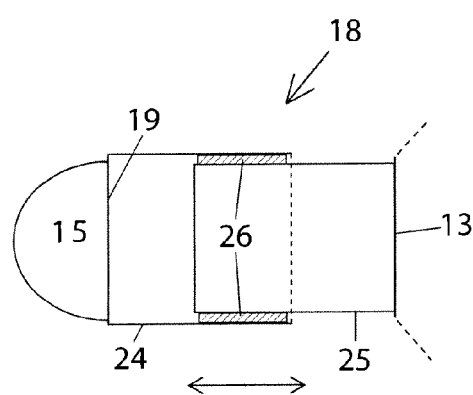
FIG. 5 is a cross-sectional view of an alternative embodiment of the spacer.

In an alternative embodiment the height of the spacer is variable. FIG. 5 is a cross-sectional view of a spacer having a variable height. In this embodiment the spacer comprises two concentrically arranged tubes 24, 25 interconnected to each other via internal and external threads 26, such that when the tubes are rotated in relation to each other the height of the spacer may be varied which is indicated in FIG. 5 by the double-arrow.

Although the present invention has been described with reference to specific embodiments it will be apparent for those skilled in the art that many variations and modifications can be performed within the scope of the invention and the invention is not limited to the embodiments described above, but is defined with reference to the claims below.

The invention claimed is:

1. A femoral compression device for compressing a femoral artery of a patient, comprising:
    a belt adapted to be arranged around a patient's body;
    a base plate comprising first and second opposing extensions, the first opposing extension having a first member configured to affix the belt at an end portion of the first opposing extension, the second opposing extension having a second member configured to affix the belt at an end portion of the second opposing extension, the first member and the second member lying in a plane, the belt traveling between the first member and the second member on a patient side of the plane;
    an inflatable air cushion, provided with a back plate, for compressive bearing against a puncture site, the air cushion being located closer to the first member than the second member;
    a pump connectable to the inflatable air cushion for inflation of the air cushion; and
    a spacer having a height and being removably mounted to the base plate via attachment members and mounted between the back plate of the inflatable air cushion and the base plate,
    wherein the spacer is removably mounted to the base plate via the attachment members at a projected portion of the base plate projecting furthest away from the plane in a direction perpendicular to the plane on the patient side of the plane, the projected portion projecting further away from the plane in a direction perpendicular to the plane on the patient side of the plane than the first and second members, wherein the inflatable air cushion is located on the patient side of the plane.

2. The femoral compression device according to claim 1, wherein the spacer has an essentially circular-cylindrical shape with a cylinder wall having first and second edges.

3. The femoral compression device according to claim 2, wherein the first edge is attached to the back plate of the air cushion and the second edge is attached to the base plate.

4. The femoral compression device according to claim 1, wherein the spacer is made from a transparent material.

5. The femoral compression device according to claim 1, wherein the height is in the range of 10-100mm.

6. The femoral compression device according to claim 1, wherein the height is variable.

7. The femoral compression device according to claim 6, wherein the spacer comprises two concentrically arranged tubes interconnected to each other via internal and external threads, such that when the tubes are rotated in relation to each other the height of the spacer is varied.

8. The femoral compression device according to claim 1, wherein the spacer is removably mounted to the back plate.

9. The femoral compression device according to claim 1, wherein the spacer contacts the back plate.

10. A femoral compression device for compressing a femoral artery of a patient, comprising:
    a belt adapted to be arranged around a patient's body;
    a base plate comprising two opposing extensions, each of the two opposing extensions having a member for affixing the belt at an end portion, the members lying in a plane, the belt traveling between the members on a patient side of the plane;
    an inflatable air cushion, provided with a back plate, for compressive bearing against a puncture site;
    a pump connectable to the inflatable air cushion for inflation of the air cushion; and
    a spacer having a height and being removably mounted to the base plate and mounted between the back plate of the inflatable air cushion and the base plate;
    wherein the spacer has an essentially circular-cylindrical shape with a cylinder wall having first and second edges;
    wherein the cylinder wall has a thinner thickness away from the first and second edges as compared to a thickness at the first and second edges,
    wherein the spacer is removably mounted to the base plate at a projected portion of the base plate projecting furthest away from the plane in a direction perpendicular to the plane on the patient side of the plane, the projected portion projecting further away from the plane in a direction perpendicular to the plane on the patient side of the plane than the members, wherein the inflatable air cushion is located on the patient side of the plane.

11. A femoral compression device for compressing a femoral artery of a patient, comprising:
    a belt adapted to be arranged around a patient's body;

a base plate comprising two opposing extensions, each of the two opposing extensions having a member for affixing the belt at an end portion, the members lying in a plane, the belt traveling between the members on a patient side of the plane;
an inflatable air cushion, provided with a back plate, for compressive bearing against a puncture site;
a pump connectable to the inflatable air cushion for inflation of the air cushion; and
a spacer having a height and being removably mounted to the base plate and mounted between the back plate of the inflatable air cushion and the base plate;
wherein the spacer has an essentially circular-cylindrical shape with a curved cylinder sidewall and first and second ends,
wherein the spacer is provided with at least one opening that passes through the curved cylinder sidewall,
wherein the spacer is removably mounted to the base plate at a projected portion of the base plate projecting furthest away from the plane in a direction perpendicular to the plane on the patient side of the plane, the projected portion projecting further away from the plane in a direction perpendicular to the plane on the patient side of the plane than the members, wherein the inflatable air cushion is located on the patient side of the plane.

12. A femoral compression device for compressing a femoral artery of a patient, comprising:
a belt adapted to be arranged around a patient's body;
a base plate comprising first and second opposing extensions, the first opposing extension having a first member configured to affix the belt at an end portion of the first opposing extension, the second opposing extension having a second member configured to affix the belt at an end portion of the second opposing extension, the first member and the second member lying in a plane, the belt traveling between the first member and the second member on a patient side of the plane;
an inflatable air cushion, provided with a back plate, for compressive bearing against a puncture site, the air cushion being located closer to the first member than the second member;
a pump connectable to the inflatable air cushion for inflation of the air cushion; and
a spacer having a height and being removably mounted to the base plate via adhesive and mounted between the back plate of the inflatable air cushion and the base plate,
wherein the spacer is removably mounted to the base plate at a projected portion of the base plate projecting furthest away from the plane in a direction perpendicular to the plane on the patient side of the plane, the projected portion projecting further away from the plane in a direction perpendicular to the plane on the patient side of the plane than the first and second members, wherein the inflatable air cushion is located on the patient side of the plane.

* * * * *